United States Patent
Emaminejad et al.

(10) Patent No.: US 10,585,096 B2
(45) Date of Patent: Mar. 10, 2020

(54) METHODS AND SYSTEMS FOR ORIENTING NANOMATERIALS

(71) Applicant: The Board of Trustees of the Leland Stanford Junior University, Palo Alto, CA (US)

(72) Inventors: Sam Emaminejad, Stanford, CA (US); Mehdi Javanmard, Sunnyvale, CA (US); Chaitanya Gupta, Foster City, CA (US); Roger T. Howe, Los Gatos, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 539 days.

(21) Appl. No.: 15/031,793

(22) PCT Filed: Oct. 24, 2014

(86) PCT No.: PCT/US2014/062136
§ 371 (c)(1),
(2) Date: Apr. 25, 2016

(87) PCT Pub. No.: WO2015/061661
PCT Pub. Date: Apr. 30, 2015

(65) Prior Publication Data
US 2016/0245807 A1    Aug. 25, 2016

Related U.S. Application Data

(60) Provisional application No. 61/895,563, filed on Oct. 25, 2013.

(51) Int. Cl.
*G01N 33/543* (2006.01)

(52) U.S. Cl.
CPC ..... *G01N 33/54393* (2013.01); *G01N 33/543* (2013.01); *G01N 33/54306* (2013.01)

(58) Field of Classification Search
CPC ....... G01N 33/54393; G01N 33/54306; G01N 33/543
See application file for complete search history.

(56) References Cited

U.S. PATENT DOCUMENTS

| | | |
|---|---|---|
| 5,466,589 A | 11/1995 | Olinger et al. |
| 7,041,343 B1 | 5/2006 | Nelles et al. |
| 2005/0069880 A1* | 3/2005 | Mamine ............... G01N 33/543 435/6.16 |
| 2009/0016924 A1 | 1/2009 | Allen et al. |
| 2012/0059156 A1 | 3/2012 | Salemme et al. |

OTHER PUBLICATIONS

International Search Report for PCT/US2014/062136 dated Jan. 12, 2015.

(Continued)

*Primary Examiner* — Rebecca L Martinez
(74) *Attorney, Agent, or Firm* — Foley & Lardner LLP; Cliff Z. Liu (57) ABSTRACT

Embodiments of the present disclosure provide for systems of enhancing the signal to noise ratio, methods of orienting a nanomaterial (e.g., an antibody), methods of enhancing the signal to noise ratio in a system (e.g., an assay system), and the like.

8 Claims, 7 Drawing Sheets

(56) References Cited

OTHER PUBLICATIONS

"Prediction of Protein Orientation Upon Immobilization on Biological and Nonbiological Surfaces," A. H. Talasaz, M. Nemat-Gorgani, Y. Liu, R Stahl, R. W. Dutton, M. Onagri, R. W. Davis, Proceedings of the National Academy of Sciences, 103, 14773 (2006).

Berk, D. A.; Yuan, F.; Leunig, M.; Jain, R. K., Fluorescence photobleaching with spatial Fourier analysis: measurement of diffusion in light-scattering media. Biophys J 1993, 65 (6), 2428-36.

Gupta, C.; Walker, R. M.; Gharpuray, R.; Shulaker, M. M.; Zhang, Z.; Javanmard, M.; Davis, R. W.; Murmann, B.; Howe, R. T. In Electrochemical quantum tunneling for electronic detection and characterization of biological toxins, Proceedings of SPIE, p. 837303.

Polk, B. J.; Stelzenmuller, A.; Mijares, G.; MacCrehan, W.; Gaitan, M., Ag/AgCl microelectrodes with improved stability for microfluidics. Sensors and Actuators B: Chemical 2006, 114, (1), 239-247.

Kanno, S.; Yanagida, Y.; Haruyama, T.; Kobatake, E.; Aizawa, M., Assembling of engineered IgG-binding protein on fold surface for highly oriented antibody immobilization. Journal of biotechnology 2000, 76, (2), 207-214.

Li, Y.; Srinivasan, B.; Jing, Y.; Yao, X.; Hugger, M. A.; Wang, J. P.; Xing, C., Nanomagnetic competition assay for low-abundance protein biomarker quantification in unprocessed human sera. J Am Chem Soc 2010, 132, (12), 4388-92.

Javanmard, M.; Talasaz, A. H.; Nemat-Gorgani, M.; Pease, F; Onagri, M.; Davis, R. W., Electrical detection of protein biomarkers using bioactivated microfluidic channels. Lab Chip 2009, 9, (10), 1429-1434.

Chen, S.; Liu, L.; Zhou, J.; Jiang, S., Controlling Antibody Orientation on Charged Self-Assembled Monolayers. Langmuir 2003, 19 (7), 2859-2864.

Lu, Y.; Liu, G. L; Kim, J.; Mejia, Y. X.; Lee, L. P., Nanophotonic crescent moon structures with sharp edge for ultrasensitive biomolecular detection by local electromagnetic field enhancement effect. Nano letters 2005, 5, (1), 119-124.

Osterfeld, S. J.; Yu, H.; Gaster, R. S.; Caramuta, S.; Xu, L; Han, S. J.; Hall, D. A.; Wilson, R. J.; Sun, S.; White, R. L.; Davis, R. W.; Pourmand, N.; Wang, S. X., Multiplex protein assays based on real-time magnetic nanotag sensing. Proc Natl Acad Sci U S A 2008, 105, (52), 20637-40.

Peluso, P.; Wilson, D. S.; Do, D.; Tran, H.; Venkatasubbaiah, M.; Quincy, D.; Heidecker, B.; Poindexter, K.; Tolani, N.; Phelan, M., Optimizing antibody immobilization strategies for the construction of protein microarrays. Analytical Biochemistry 2003, 312, (2), 113-124.

Xu, Z.; Chen, Y.; Gartia, M. R.; Jiang, J.; Liu, G. L., Surface plasmon enhanced broadband spectrophotometry on black silver substrates. Applied Physics Letters 98, (24), 241904-241904-3.

Mulvaney, S. P.; Myers, K. M.; Sheehan, P. E.; Whitman, L. J., Attomolar protein detection in complex sample matrices with semi-homogeneous fluidic force discrimination assays. Biosensors and Bioelectronics 2009, 24, (5), 1109-1115.

Lu, Y.; Liu, G. L.; Lee, L. P., High-density silver nanoparticle film with temperature-controllable interparticle spacing for a tunable surface enhanced Raman scattering substrate. Nano letters 2005, 5, (1), 5-9.

Squires, T. M.; Messinger, R. J.; Manalis, S. R., Making it stick: convection, reaction and diffusion in surface-based biosensors. Nature biotechnology 2008, 26, (4), 417-426.

Kim, Y.-G.; Moon, S.; Kuritzkes, D. R.; Demirci, U., Quantum dot-based HIV capture and imaging in a microfluidic channel. Biosensors and Bioelectronics 2009, 25, (1), 253-258.

Wang, H.; Chen, Y.; Hassibi, A.; Scherer, A.; Hajimiri, A. In a frequency-shift CMOS magnetic biosensor array with single-bead sensitivity and no external magnet, Solid-State Circuits Conference—Digest of Technical Papers, 2009. ISSCC 2009. IEEE International, 2009; IEEE: 2009; pp. 438-439,439 a.

Jeanmaire, D. L.; Van Duyne, R. P., Surface Raman spectroelectrochemistry: Part I. Heterocyclic, aromatic, and aliphatic amines adsorbed on the anodized silver electrode. Journal of Electroanalytical Chemistry and Interfacial Electrochemistry 1977, 84, (1), 1-20.

Zhou, J.; Tsao, H.-K; Sheng, Y.-J.; Jiang, S., Monte Carlo simulations of antibody adsorption and orientation on charged surfaces. The Journal of Chemical Physics 2004, 121 (2), 1050-1057.

Zhu, H.; Snyder, M., Protein chip technology. Current opinion in chemical biology 2003, 7, (1), 55-63.

\* cited by examiner

METHODS AND SYSTEMS FOR ORIENTING NANOMATERIALS

CLAIM OF PRIORITY TO RELATED APPLICATION

This application is the 35 U.S.C. § 371 national stage application of PCT Application No. PCT/US2014/062136, filed Oct. 24, 2014, which claims priority to U.S. provisional application entitled "METHODS AND SYSTEMS FOR ORIENTING NANOMATERIALS" having Ser. No. 61/895,563, filed on Oct. 25, 2013, both of which are entirely incorporated herein by reference.

FEDERAL SPONSORSHIP

This invention was made with Government support under Contract/Grant No. N66001-11-1-4111 awarded by the Defense Advanced Research Projects Agency. The Government has certain rights in this invention.

BACKGROUND

Immobilization of proteins on solid surfaces has wide application in various types of biosensing platforms. Both affinity based sensing platforms and probe-free biosensors can benefit from controlled orientation of proteins during immobilization on sensing surfaces. Thus, there is a need to address orientation for biosensing platforms.

SUMMARY

Embodiments of the present disclosure provide for systems of enhancing the signal to noise ratio, methods of orienting a nanomaterial (e.g., an antibody), methods of enhancing the signal to noise ratio in a system (e.g., an assay system), and the like.

An embodiment of the method of orienting a nanomaterial, among others, includes: exposing a solution including the nanomaterial to a substrate; applying an electric field to the substrate (e.g., lateral to the substrate); uniformly orienting the nanomaterial on the surface of the substrate; and immobilizing the nanomaterial to the surface of the substrate so that the nanomaterials are uniformly aligned on the surface of the substrate.

An embodiment of the method of enhancing the signal to noise ratio in a system, among others, includes: applying an electric field to a substrate, wherein a solution including a nanomaterial is disposed on the substrate, wherein the electric field causes the nanomaterials to uniformly orientate and align on the surface of the substrate; wherein an enhanced signal to noise ratio is produced as compared to an otherwise identical system that does apply the electric field.

An embodiment of the system, among others, includes: a substrate, wherein a nanomaterial has an affinity for a surface of the substrate; and an electric field system configured to apply an electric field to the substrate to uniformly orientate and align the nanomaterial on the surface of the substrate, wherein the system is configured to produce an enhanced signal to noise ratio than an otherwise identical system that does include the electric field system.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1.1A illustrates antibodies (IgG) having an $F_c$ region and an $F_{ab}$ region where the isoelectric point of the $F_{ab}$ region is higher compared to the $F_c$ region resulting in dipole behavior. FIG. 1.1B illustrates the antibody reorients itself in the direction of the electric field. FIG. 1.1C illustrates an immobilized mouse IgG on the surface and detection of the molecule by attachment of anti-mouse IgG molecules linked to micron-sized beads. FIG. 1.1D illustrates immobilized goat IgG on the surface and detection of the molecule by attachment of FITC labeled anti-goat IgG.

FIG. 1.2 illustrates a schematic of the fluorescent assay experimental setup. Field is modulated during the goat IgG immobilization. When electric field is off IgG molecules are randomly oriented. When field is on, IgG molecules are oriented on their sides so that the $F_c$ region is exposed allowing an increase in binding of anti-goat IgG molecules.

FIG. 1.3A illustrates a bead based assay where electric field is on and off. FIG. 1.3B illustrates a fluorescent based assay where electric field is on and off. FIG. 1.3C illustrates the relationship of signal intensity versus voltage applied across microchannel.

FIG. 1.4 illustrates a comparison of antibody coated surface when field is off during immobilization to when field is. FIGS. 1.4A and 1.4B illustrates a two dimensional and three dimensional AFM image for when field is off. FIG. 1.4C and 1.4D illustrate two dimensional and three dimensional AFM image for when field is on. Results indicated that field results in antibodies orienting in a uniform direction.

FIG. 2.1 illustrate a bead-based multiplexed immunoassay.

FIG. 2.2 illustrates the corresponding raw video snapshots of the beads distribution before after turning negative DEP on.

FIG. 2.3 illustrates the titration curve for Abl Kinase concentration in purified buffer.

FIG. 2.4 illustrates the comparison of antibody coated surface (AFM imaging) when field is off during antibody immobilization vs. when field is on.

FIG. 2.5 illustrates an AFM image and analysis of antibody coated surface when field is on during antibody immobilization (IgG concentration of 10 µg/ml).

FIG. 2.6 illustrates the AFM image and analysis of antibody coated surface when field is off and on during antibody immobilization.

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of chemistry, material science, and the like, which are within the skill of the art. Such techniques are explained fully in the literature.

The following examples are put forth so as to provide those of ordinary skill in the art with a complete disclosure and description of how to perform the methods and use the structures disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Definitions

In describing and claiming the disclosed subject matter, the following terminology will be used in accordance with the definitions set forth below.

As used herein, the terms "antibody" and "antibodies" can include, but are not limited to, monoclonal antibodies, multispecific antibodies, human antibodies, humanized antibodies, camelised antibodies, chimeric antibodies, single-chain Fvs (scFv), single chain antibodies, Fab fragments, F(ab') fragments, disulfide-linked Fvs (sdFv), and anti-idiotypic (anti-Id) antibodies (e.g., anti-Id antibodies to antibodies of the disclosure), and epitope-binding fragments of any of the above. The antibodies may be monospecific, bispecific, trispecific, or of greater multispecificity.

As used herein, "antigen" describes a compound, a composition, or a substance that can stimulate the production of antibodies or a T-cell response in a host.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

As used herein, the term "polynucleotide" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompasses a polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alias.

"Aptamers" may be high affinity, high specificity polypeptide, RNA, or DNA-based probes produced by in vitro selection experiments. Aptamers may be generated from random sequences of nucleotides or amino acids, selectively screened by absorption to molecular antigens or cells, and enriched to purify specific high affinity binding ligands, for example. In solution, aptamers may be unstructured but may fold and enwrap target epitopes providing specific binding recognition. The unique folding of the nucleic acids around the epitope, for example, affords discriminatory intermolecular contacts through hydrogen bonding, electrostatic interaction, stacking, and shape complementarity.

Use of the phrase "biomaterial" or "biomolecule" is intended to encompass at least deoxyribonucleic acid (DNA), ribonucleic acid (RNA), nucleotides, oligonucleotides, nucleosides, polynucleotides, proteins, peptides, polypeptides, selenoproteins, antibodies, antigens, protein complexes, aptamers, combinations thereof, and the like.

Use of "biological target" is intended to encompass biomolecules (e.g., deoxyribonucleic acid (DNA), ribonucleic acid (RNA), nucleotides, oligonucleotides, nucleosides, polynucleotides, proteins, peptides, polypeptides, selenoproteins, antibodies, antigens, protein complexes, aptamers, combinations thereof), and the like. In particular, biological target can include, but is not limited to, naturally occurring substances such as polypeptides, polynucleotides, lipids, fatty acids, glycoproteins, carbohydrates, fatty acids, fatty esters, macromolecular polypeptide complexes, vitamins, co-factors, whole cells, eukaryotic cells, prokaryotic cells, micelles, microorganisms such as viruses, bacteria, protozoa, archaea, fungi, algae, spores, apicomplexan, trematodes, nematodes, mycoplasma, or combinations thereof. In addition, the biological target can include native intact cells, viruses, bacterium, and the like.

Use of the term "affinity" can include biological interactions and/or chemical interactions. The biological interactions can include, but are not limited to, bonding or hybridization among one or more biological functional groups located on the first biomolecule or biological target and the second biomolecule or biological target. The chemical interaction can include, but is not limited to, bonding among one or more functional groups (e.g., organic and/or inorganic functional groups) located on the biomolecules.

The term "array" encompasses the term "microarray" and refers to an ordered array presented for binding to polynucleotides, polypeptides, protein, antibodies, antigens, and the like.

An "array" includes any two-dimensional or substantially two-dimensional (as well as a three-dimensional) arrangement of addressable regions including biomolecules and the like. Where the arrays are arrays of biomolecules, the biomolecules may be adsorbed, physisorbed, chemisorbed, and/or covalently attached to the arrays at any point or points of the biomolecule.

A substrate may carry one, two, four or more arrays disposed on a front surface of the substrate. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than about 20 cm$^2$ or even less than about 10 cm$^2$ (e.g., less than about 5 cm$^2$, including less than about 1 cm$^2$ or less than about 1 mm$^2$ (e.g., about 100 μm$^2$, or even smaller)). For example, features may have widths (that is, diameter, for a round spot) in the range from about 10 μm to 1.0 cm.

Arrays can be fabricated using drop deposition from pulse-jets of either polynucleotide precursor units (such as monomers), in the case of in situ fabrication, or the previously obtained nucleic acid. Such methods are described in detail, for example, in U.S. Pat. Nos. 6,242,266, 6,232,072, 6,180,351, 6,171,797, and 6,323,043. As already mentioned, these references are incorporated herein by reference.

An array "package" may be the array plus a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and 'lower" are used in a relative sense only.

An array is "addressable" when it has multiple regions of the same or different moieties (e.g., different biomolecules) such that a region (i.e., a "feature" or "spot" of the array) at a particular predetermined location (i.e., an "address") on the array can detect a particular biomolecule. Array features are typically, but need not be, separated by intervening spaces. In the case of a type of an array in the context of the present application, the "target" will be referenced in certain embodiments as a moiety in a mobile phase (typically fluid), to be detected by "biomolecules," which are bound to the substrate at the various regions.

A "scan region" refers to a contiguous (preferably, rectangular) area in which the array spots or features of interest, as defined above, are found or detected. The scan region is that portion of the total area queried from which resulting signal is detected and recorded.

An "array layout" refers to one or more characteristics of the features, such as feature positioning on the substrate, one or more feature dimensions, and an indication of a moiety at a given location.

Discussion:

Embodiments of the present disclosure provide for systems of enhancing the signal to noise ratio, methods of orienting a nanomaterial (e.g., an antibody), methods of enhancing the signal to noise ratio in a system (e.g., an assay system), and the like. Embodiments of the present disclosure provide for the controlled orientation and immobilization of a nanomaterial using an electric field so that the nanomaterials are uniformly oriented and aligned. Embodiments of the present disclosure can enhance sensitivity and reduce the signal to noise ratio.

An embodiment of the present disclosure provides for a method of orienting and aligning a nanomaterial in a controllable manner on a substrate. In an embodiment, the substrate can be used in an optical, electronic, and/or magnetic platform, such as a biosensing platform. In an embodiment, the substrate can be used in a probe or a probe-free platform. In an embodiment, the substrate can be used in an affinity-based platform. In an embodiment, the substrate can be used in an assay system. In an embodiment, the substrate can be used in an array having a plurality of addressable locations.

In an embodiment, the substrate is exposed to a solution that includes the nanomaterial. In an embodiment, the substrate can include addressable locations to dispose the nanomaterials. For example, the addressable locations on the substrate can include an agent that has an affinity for the nanomaterial or a particular portion of the nanomaterial (e.g., a moiety). In an embodiment, the agent can include: an agent with a functional group that preferentially reacts with a portion of the nanomaterial. In an embodiment, the agent can include: a protein, an antibody (monoclonal or polyclonal), an antigen, a polynucleotide, a hapten, a polysaccharide, a sugar, a fatty acid, a steroid, a purine, a pyrimidine, a ligand, an aptamer, a small molecules, a ligand, or combinations thereof.

In an embodiment, the substrate does not include addressable locations, so that the nanomaterials randomly (in regard to location) bond to the surface of the substrate. In an embodiment, the nanomaterials can bond to the substrate directly or indirectly via an agent such as those described above.

In an embodiment, the substrate can include a material that can be used to attach (e.g., be bound to the substrate) to (directly or indirectly) the nanomaterial. In an embodiment, the substrate can include a solid-state substrate and the like. In an embodiment, the solid-state substrate can be made of a material such as glass, semiconductor material, and the like.

In general, the nanomaterial can be: a biological target that is to be detected (directly or indirectly), used to be a linker to another agent, used to attract a biological target to be detected, or the like. In an embodiment, the nanomaterial can have an affinity for an agent that is to be detected, an affinity for the substrate or another agent disposed on the substrate, or the like. In an embodiment, the nanomaterial can include materials such as biomaterials, biological targets, and the like. In an embodiment, the biomaterial can include a protein, an antibody (monoclonal or polyclonal), an antigen, a polynucleotide, a hapten, a polysaccharide, a sugar, a fatty acid, a steroid, a purine, a pyrimidine, a ligand, an aptamer, a small molecules, a ligand, or combinations thereof.

In an embodiment, the nanomaterial can also include an imaging tag such as an optical tag, a magnetic tag, an electronic tag, and the like. In an embodiment, the nanomaterial can also include a dye, a quantum dot, a magnetic particle, a fluorescent particle or compound, and the like, so that the presence of the biomaterial can be detected.

Once the solution is exposed to the substrate, an electric field is applied to the substrate. In an embodiment, the electric field is applied in such a manner so as to cause the desired orientation of the nanomaterial relative to the substrate. In an embodiment, the electric field is applied laterally across the substrate. In an embodiment, the electric field can be applied at an angle (e.g., about 0 to 180°, and each angle within the range) to the substrate. In an embodiment, the electric field is applied using an electric field system such as those known in the art.

As mentioned above, the electric field causes the nanomaterials to uniformly orientate themselves on the surface of the substrate. Once, or as the nanomaterials orientate themselves on the surface of the substrate, the nanomaterial becomes immobilized on the surface so that the nanomaterials are uniformly aligned on the surface of the substrate via one or more bonds or interactions. In an embodiment, about 70% or more, about 80% or more, about 90% or more, about 95% or more, or about 99% or more, of the nanomaterials are orientated in the same or substantially the same direction, where the angle of orientation of the nanomaterial relative to the surface is about 20 to 160° or about 70 to 120°. In an embodiment, the nanomaterials can be bound (directly or indirectly) to the surface by a physical, biological, biochemical, and/or chemical association. The term "bound" can include, but is not limited to, chemically bonded (e.g., covalently or ionically), biologically bonded, biochemically bonded, and/or otherwise associated with the particle. In an embodiment, bound can include, but is not limited to, a covalent bond, a non-covalent bond, an ionic bond, a chelated bond, as well as being bound through interactions such as, but not limited to, hydrophobic interactions, hydrophilic interactions, charge-charge interactions, π-stacking interactions, combinations thereof, and like interactions.

A simple illustrative example includes a nanomaterial having a side A and a side B. If allowed to randomly become immobilized on the surface, side A may be adjacent the substrate and side B positioned away from the substrate and vice versa for some nanomaterials. In contrast, when an electric field is applied to the substrate, the electric field causes the nanomaterial to orientate so side A is towards the substrate and side B is away from the substrate for a substantial portion (e.g., about 75% or more, about 80% or more, about 85% or more, about 90% or more, about 95% or more, or about 99% or more) of the nanomaterials.

In a more specific example, the nanomaterial is an antibody that includes an epitope that is more sensitive to a target to be detected. In accordance with the present disclosure, the epitope can be orientated so that the region is more accessible to a target. In addition, a substantial portion of the antibodies are orientated with an epitope in a more accessible position to the target. In this way, the sensitivity can be increased and the signal to noise to ratio can be increased relative to an otherwise identical system than does not include the electric field.

In an embodiment, the nanomaterial can be orientated based on the dipole moment of the nanomaterial, position of chemical groups, moieties, epitopes, binding sites, or the like, and a combination thereof, which can be caused directly or indirect by the applied electric field. In an embodiment, the orientation can be tuned (in combination with the electric field) by changes in pH to the solution, inclusion of one or more charged moieties on the nanomaterial, net charge of the substrate surface, three-dimensional configuration of the nanomaterial (e.g., protein structure), and a combination thereof.

Embodiments of the present disclosure can be used to enhance the signal to noise ratio in a system. For example, an electric field can be applied to a substrate. A solution including a nanomaterial is disposed on the substrate, where the electric field causes the nanomaterials to uniformly orientate and align on the surface of the substrate, as described herein. An enhanced signal to noise ratio is produced as compared to an otherwise identical system that does apply the electric field.

Embodiments of the present disclosure include a system that has a substrate and an electric field system. A nanomaterial having an affinity for a surface of the substrate is introduced to the substrate and an electric field (e.g., a DC field or an AC field) can be applied to the substrate to uniformly orientate and align the nanomaterial on the surface of the substrate. In an embodiment, the system can be configured to produce an enhanced (e.g. improved (e.g., the signal is increased relative to the noise)) signal to noise ratio than an otherwise identical system that does include the electric field system. In an embodiment, the system can be part of an array or assay system and defined herein.

While embodiments of the present disclosure are described in connection with the Example and the corresponding text and figures, there is no intent to limit the disclosure to the embodiments in these descriptions. On the contrary, the intent is to cover all alternatives, modifications, and equivalents included within the spirit and scope of embodiments of the present disclosure.

Example 1

Introduction:

Controlled immobilization of proteins on solid-state surfaces can play an important role in enhancing the sensitivity of both affinity based biosensors and probe-free sensing platforms. In this Example we present a novel method of tunably controlling the immobilization of proteins on a solid-state surface using electric field. Our study demonstrates that the use of electric field can result in up to 40× enhancement in signal to noise ratio compared to normal physical adsorption. We used atomic force microscopy to verify that the application of electric field results in modulation of the orientation of antibodies during immobilization.

Immobilization of proteins on solid surfaces has wide application in various types of biosensing platforms. Both affinity based sensing platforms [1] and probe-free biosensors [2] can benefit from controlled orientation of proteins during immobilization on sensing surfaces. In the case of affinity-based sensors, the probe protein has specific sites or epitopes where binding occurs. Probe antibody orientation during immobilization onto the surface can affect the efficiency of the capture of target analytes. This is typically performed by modifying the surface chemistry and also the functional groups on the protein of interest [3]. For probe-free sensors, uniform immobilization of target proteins on the surface will result in an amplified signal and sensitivity enhancement due to consistency of the motif attached to the surface.

Figure 11:
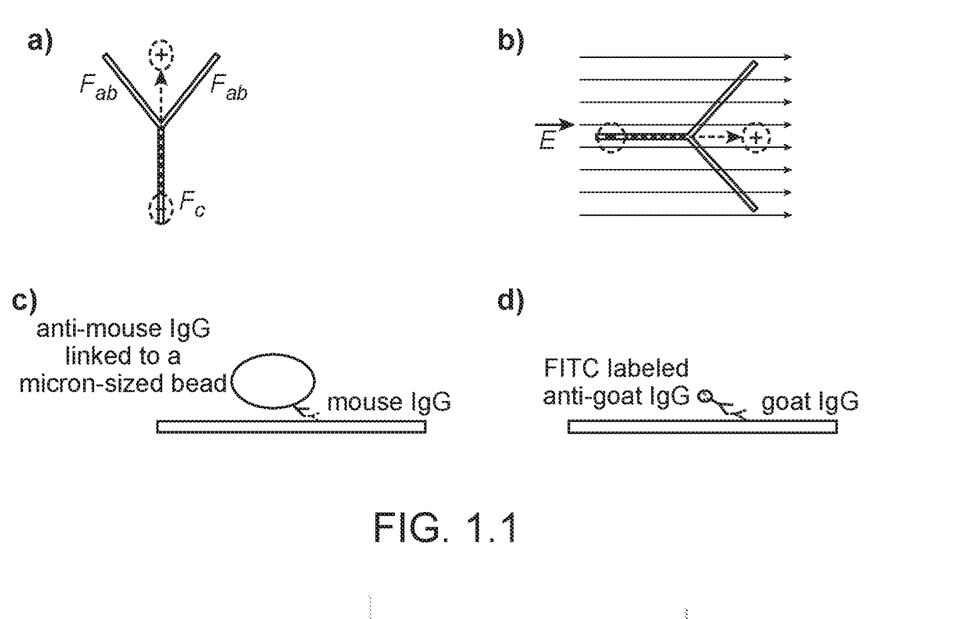
Figure 12:
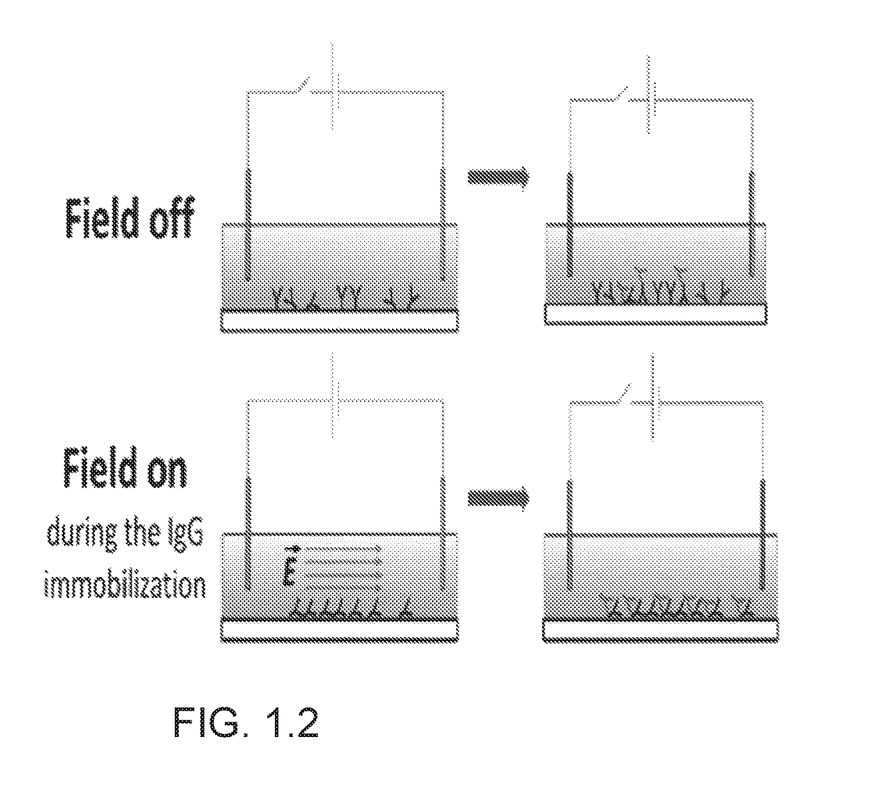
Figure 13:
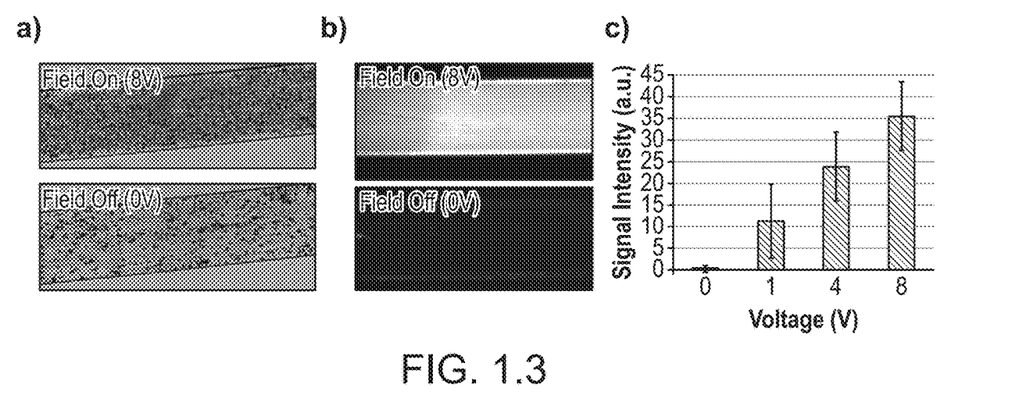
Figure 14:
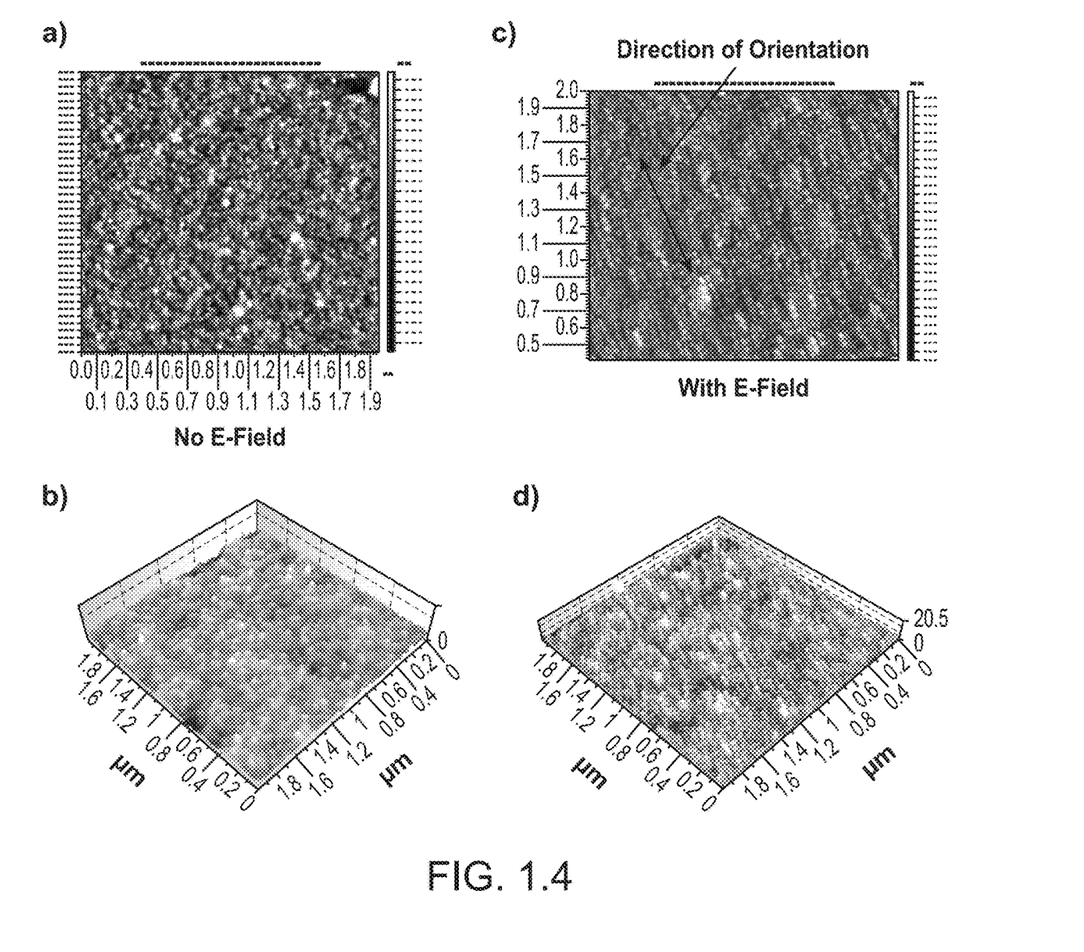

Theory:

Previously Talasaz et. al [4] developed a simulation procedure to predict the orientation of a protein related to its immobilization affected by the electric field at a solid-state support. Here, we present a novel method of tunably controlling the immobilization of proteins on a solid-state surface using electric field. We exploit the dipole property of IgG [5] and its ability to be oriented with field (FIG. 1.1A, B).

Experimental:

As a proof of concept, we use fluorescence detection to indirectly verify the modulation of the orientation of proteins bound to the surface. We studied the interaction of fluorescently tagged anti-IgG with surface immobilized IgG, where immobilization process was controlled by electric field. Our study demonstrates that the use of electric field can result in up to 40× enhancement in signal to noise ratio compared to normal physical adsorption.

To quantify the effect of the applied field on the response of the immunoassay, we use two different readout formats. In the first approach, we used anti-IgG conjugated micron-sized beads (FIG. 1.1C) to perform a bead-based assay, and in the other, we used FITC labeled anti-IgG (FIG. 1*d*) to perform a fluorescence assay. IgG (0.02 mg/ml) molecules were immobilized via physical adsorption on the surface of the microchannel (fabricated in PDMS 200 µm wide, 50 µm high, and 1 cm long). An electric field was applied during the immobilization step (FIG. 1.2). We inserted Ag—AgCl pellet electrodes at the inlet and outlet ports of the microchannel. We excited the electrodes with DC voltages up to 8 V as shown in FIG. 1.3. We independently optically verified that the voltages were not high enough to induce either electro-osmotic flow or electrophoretic flow.

Results and Discussion:

We used fluorescence imaging to quantify signal enhancement resulting from electric field. All positive and negative control experiments were performed in parallel. Our negative control was the case where no electrodes were inserted in the channel during IgG immobilization. The representative captured snapshots from our experiments illustrate the enhancement in the binding of anti-IgG and IgG as a result of applying lateral electric field during IgG immobilization, for both bead-based (FIG. 1.3A) and fluorescence (FIG. 1.3B) assays. The collective results for the fluorescence assay are presented in FIG. 1.3C, which shows the improvement in signal intensity (with respect to the control experiment) as we increased the applied voltage. We have also used atomic force microscopy (AFM) to directly verify the modulation of orientation during IgG immobilization. We compare an antibody coated surface when field is on (FIG. 1.4A, B) and off (FIG. 1.4C, D) during the immobilization step. Results indicate that the antibodies become oriented in a specific direction when field is applied.

Conclusion:

We have developed a novel technique for controlling the orientation of protein immobilization using electric field, which we have indirectly verified using a fluorescent antibody binding assay, and also directly verified using AFM. This technique can be used to improve the sensitivity of affinity based assays, and to lower their cost due to reduction in the quantity of probe antibody required for immobilization. This technique can also be useful for improving consistency and even enhancing sensitivity (e.g., improving the signal relative to the noise) of probe free assays. Future efforts will be placed on studying the utility of electric field using different structures to control the approach and orientation of proteins in various directions.

REFERENCES, each of which is incorporated herein by reference

[1] M. Javanmard, A. H. Talasaz, M. Nemat-Gorgani, F. Pease, M. Ronaghi, R. W. Davis, Electrical Detection of Protein Biomarkers Using Bioactivated Microfluidic Channels. Lab. Chip., vol. 9, pp. 1429, 2009.

[2] A. H. Talasaz, M. Nemat-Gorgani, Y. Liu, P. Stahl, R. W. Dutton, M. Ronaghi, R. W. Davis, "Prediction of Protein Orientation Upon Immobilization on Biological and Non-biological Surfaces," Proc. Natl Acad Sci, vol. 103, pp. 14773, 2006.

[3] S. Chen, L. Liu, J. Zhou, S. Jiang, Controlling Antibody Orientation on Charged Self-Assembled Monolayers. Langmuir, vol. 19, pp. 2859, 2003.

[4] C. Gupta, R. M. Walker, R. Gharpuray, M. M. Shulaker, Z. Zhang, M. Javanmard, R. W. Davis, B. Murmann, R. T. Howe. Electrochemical quantum tunneling for electronic detection and characterization of biological toxins, Proc. of SPIE, p 837303.

[5] J. Zhou, H.-K. Tsao, Y.-J. Sheng, S. Jiang, Monte Carlo simulations of antibody adsorption and orientation on charged surfaces. J. Chem. Phys., vol. 121, pp. 1050, 2004.

Example 2

Figure 21:
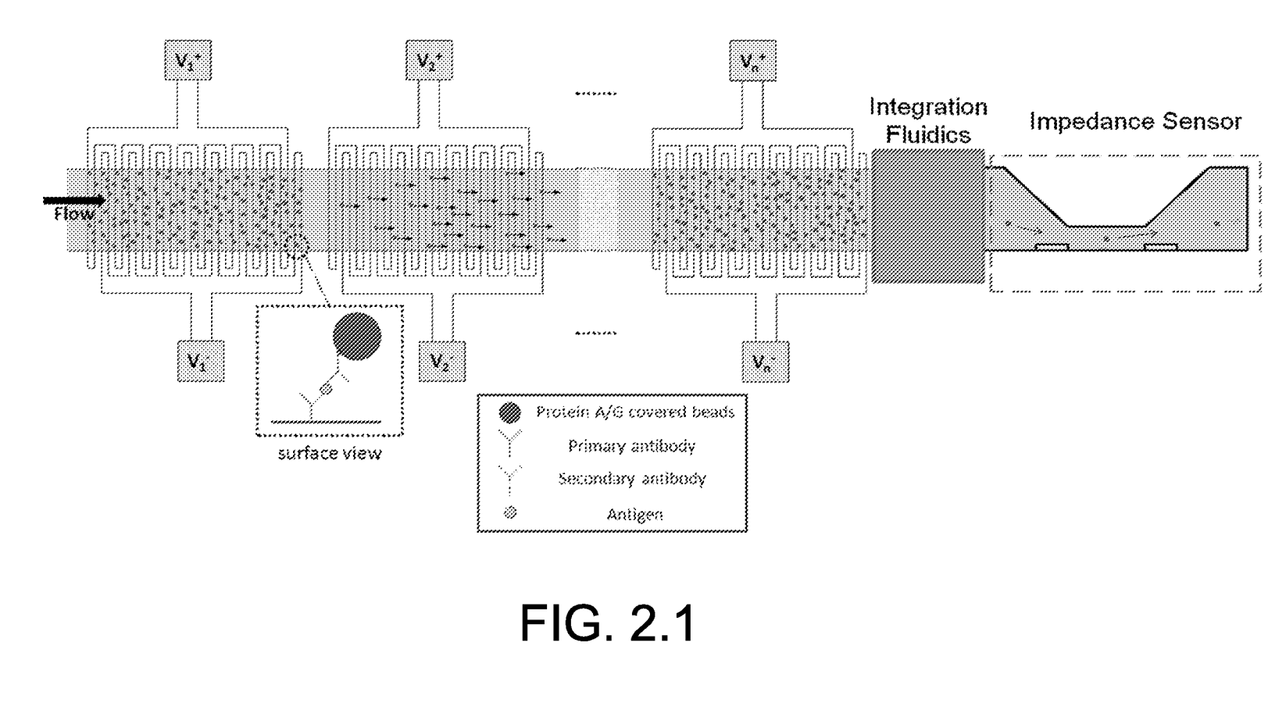

FIG. 2.1 illustrate a bead-based multiplexed immunoassay. Each element of array in the capture region is functionalized with a different antibody, each targeting a specific antigen in the sample. Specifically bound beads on each element of the array are eluted selectively from the array and are quantified downstream electrically (one element at a time). Here, applying voltage V2 produces negative DEP force, which in turn detaches the specifically bound beads from the surface of the 2nd interdigitated electrode pair. With no voltage applied at the other interdigitated electrodes, the immunobound beads on the respective elements remain attached to the surface.

Figure 22:
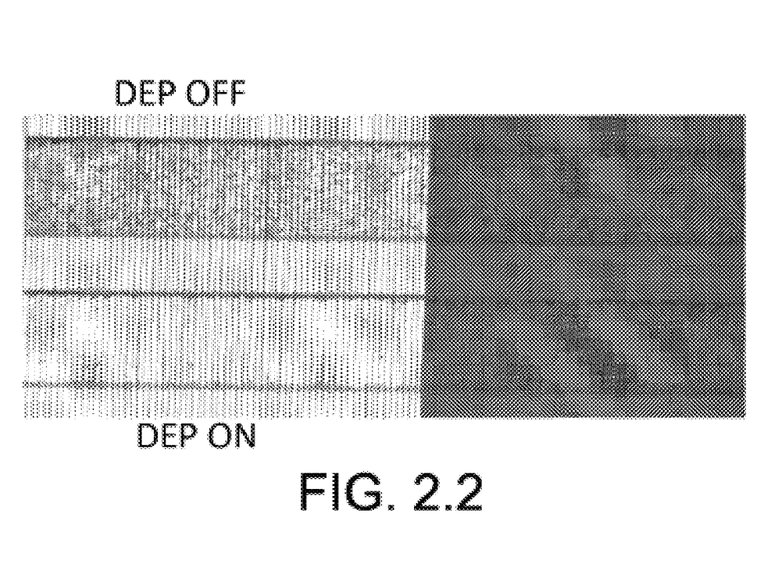

FIG. 2.2 illustrates the corresponding raw video snapshots of the beads distribution before after turning negative DEP on. The remaining beads on the electrode region are actually detached and are passing through. Similarly, the small difference between the two non-electrode regions (in 'before' and 'after' snapshots) are mainly due to the moving beads passing by (but appearing as stationary in a single frame) as verified by the image-processing software.

Figure 23:
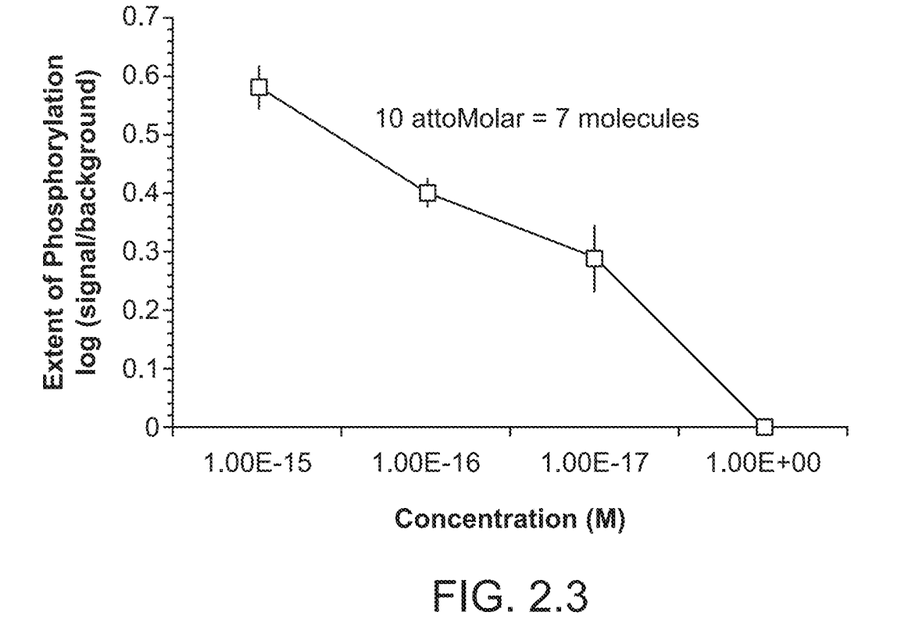

FIG. 2.3 illustrates the titration curve for Abl Kinase concentration in purified buffer. The number of beads in each channel was counted optically, and divided by number of beads nonspecifically bound in channel with no kinase. Detection limit of 10 aM ($12 \times 10^{-24}$ moles=7 molecules) achieved, with dynamic range of five orders of magnitude.

Figure 24:
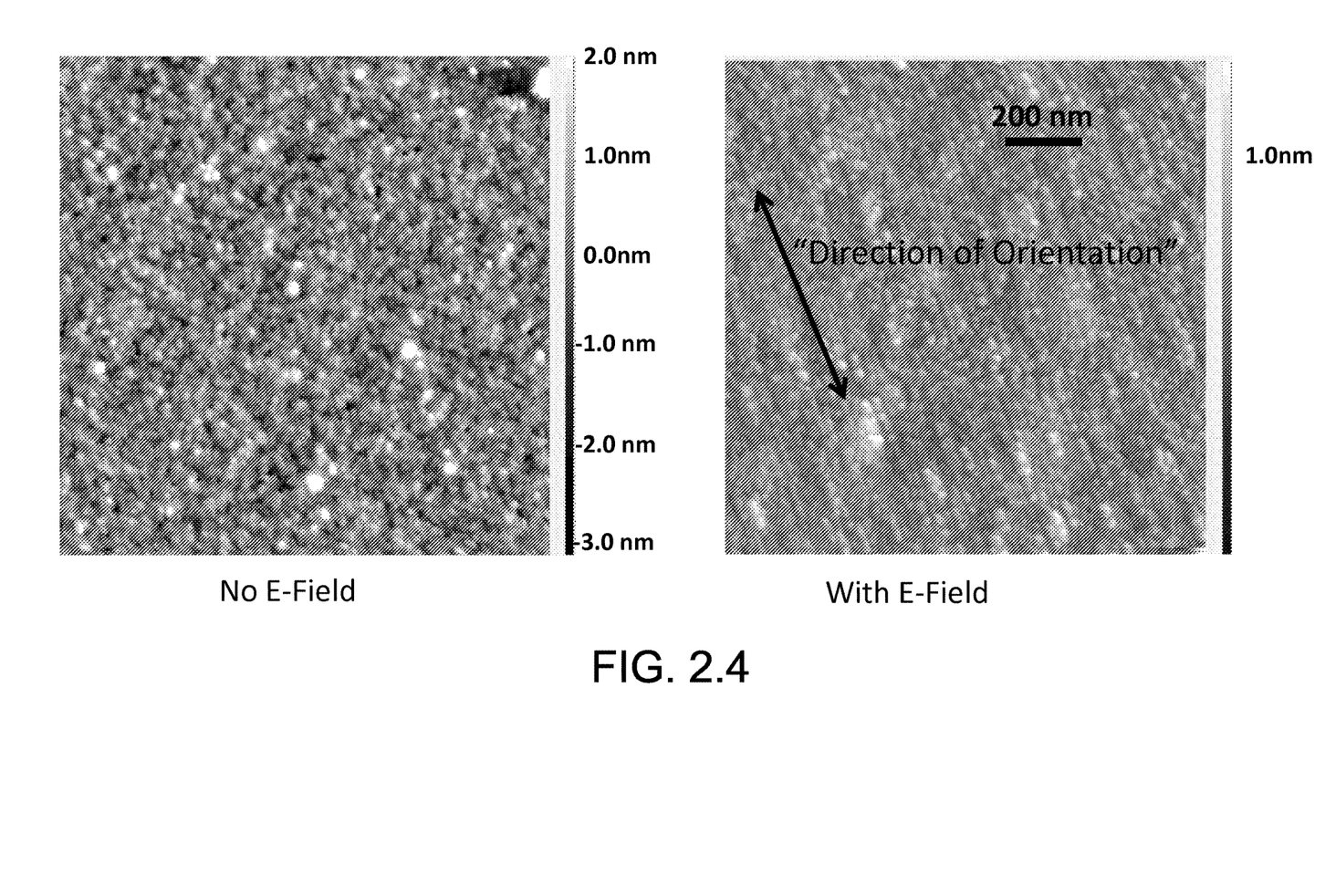

FIG. 2.4 illustrates the comparison of antibody coated surface (AFM imaging) when field is off during antibody immobilization vs. when field is on. AFM results indicate that for the case with field on during immobilization, antibodies orient in a uniform direction.

Figure 25:
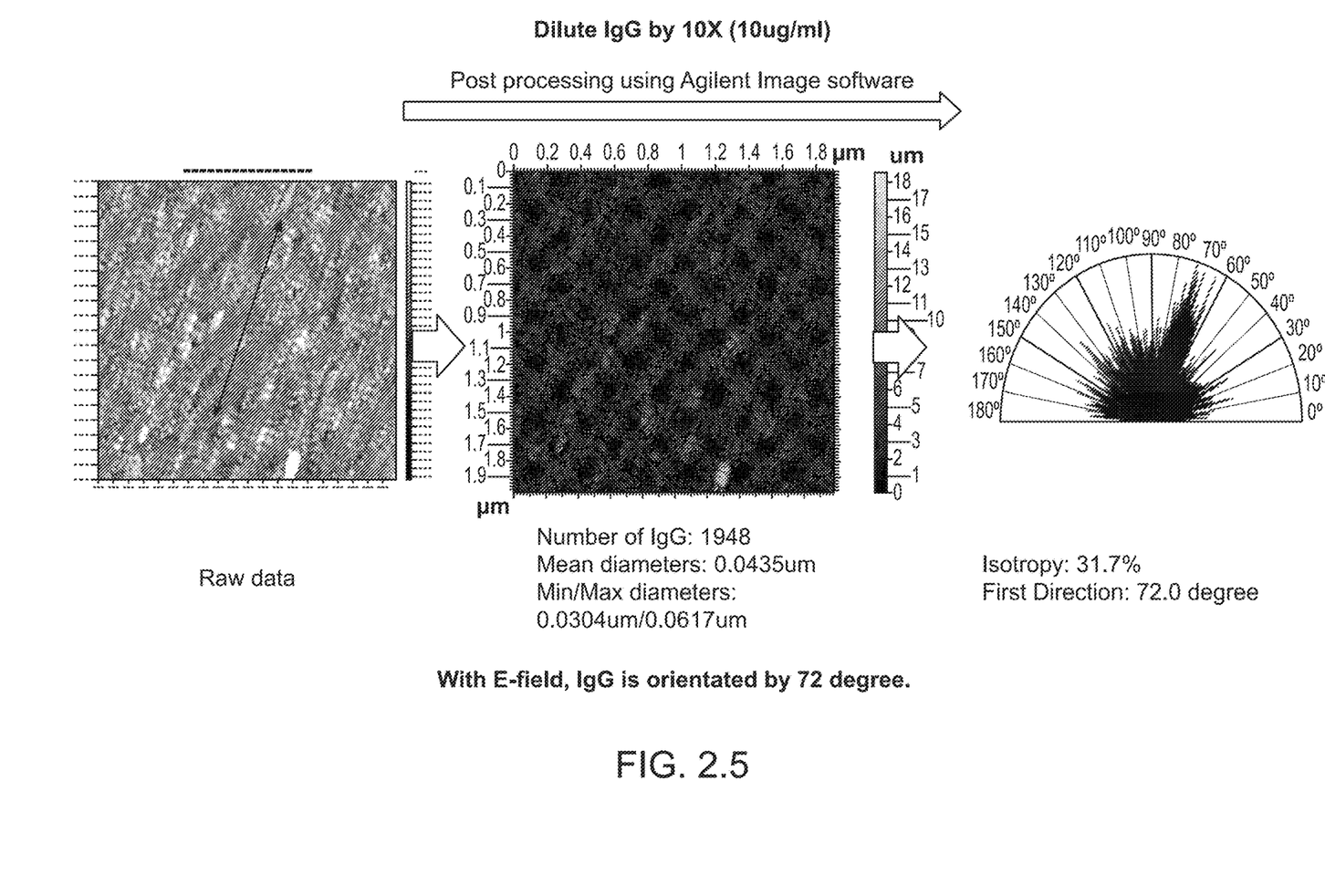

FIG. 2.5 illustrates an AFM image and analysis of antibody coated surface when field is on during antibody immobilization (IgG concentration of 10 μg/ml). The analysis indicates that a dominant orientation (72 degrees) is evident.

Figure 26:
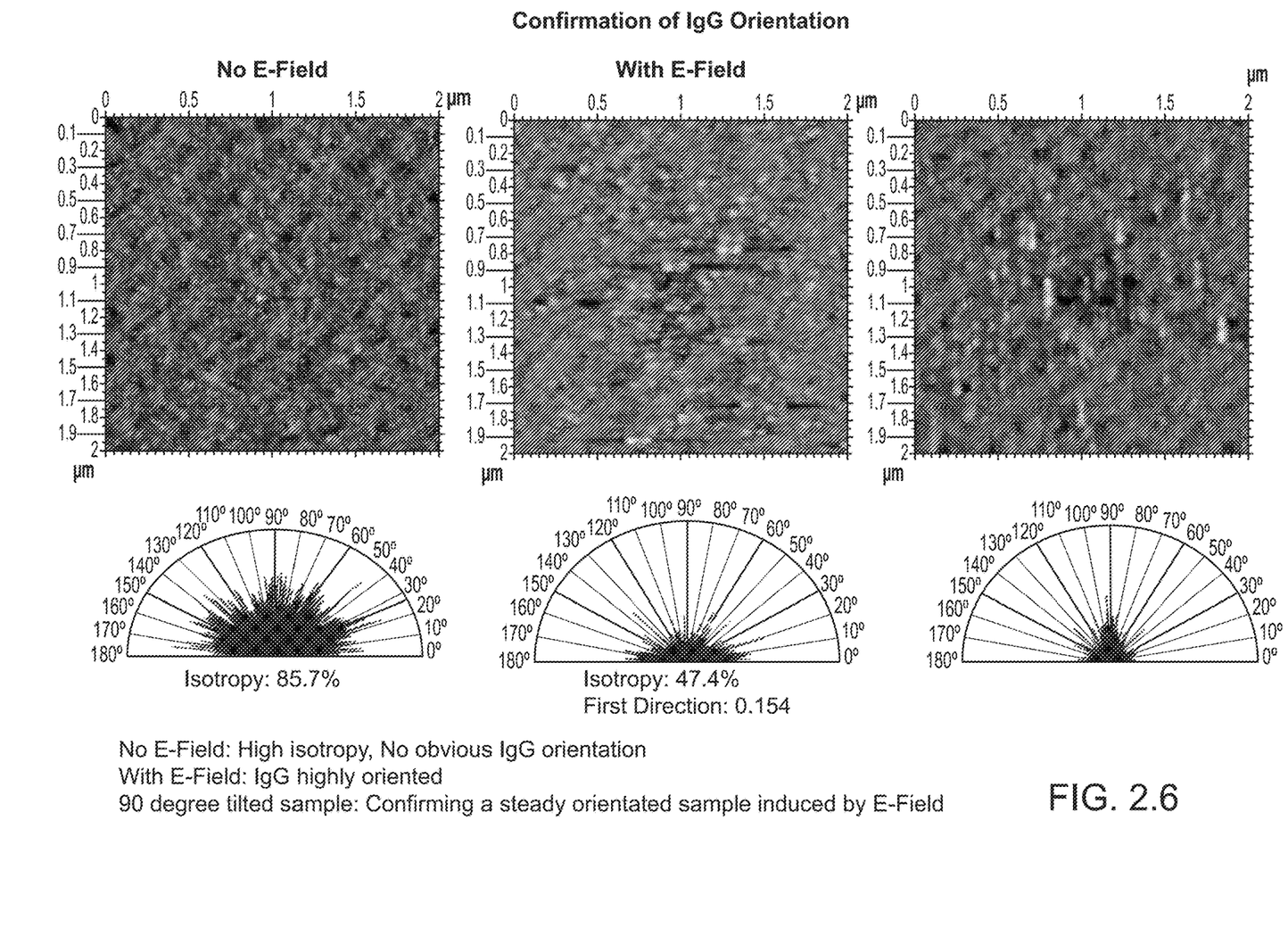

FIG. 2.6 illustrates the AFM image and analysis of antibody coated surface when field is off and on during antibody immobilization. For the case with no electric field, there is no dominant orientation, while for the case with electric field, a dominant orientation (0 degree) is evident. The surface of the 'sample with electric field' is rotated 90 degrees to ensure that the dominant orientation also rotates by 90 degrees. Our AFM analysis confirms the 90 degree rotation.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

While only a few embodiments of the present disclosure have been shown and described herein, it will become apparent to those skilled in the art that various modifications and changes can be made in the present disclosure without departing from the spirit and scope of the present disclosure. All such modification and changes coming within the scope of the appended claims are intended to be carried out thereby.

We claim at least the following:

1. A method of orienting a nanomaterial, comprising:
    exposing a solution including the nanomaterial to a substrate; and
    immobilizing the nanomaterial to a surface of the substrate while applying an electric field adjacent to and laterally across the surface of the substrate, so that the nanomaterial is uniformly aligned and immobilized on the surface of the substrate.

2. The method of claim 1, wherein the substrate is a solid-state substrate.

3. The method of claim 2, wherein the nanomaterial is a biomaterial.

4. The method of claim 3, wherein the biomaterial is selected from the group consisting of: a polypeptide, a protein, an antibody, an antigen, and a polynucleotide.

5. The method of claim 1, wherein immobilizing includes orienting 70% or more of the nanomaterial disposed on the surface of the substrate.

6. The method of claim 1, wherein an angle of orientation of the nanomaterial relative to the surface is 70 to 120°.

7. The method of claim 1, wherein immobilizing includes orienting 70% or more of the nanomaterial disposed on the surface of the substrate, wherein an angle of orientation of the nanomaterial relative to the surface is 70 to 120°, and wherein the nanomaterial is a biomaterial selected from the group consisting of: a polypeptide, a protein, an antibody, an antigen, and a polynucleotide.

8. The method of claim 1, wherein an orientation of the nano material is maintained after turning off the electric field.

* * * * *